(12) United States Patent
Hafemann

(10) Patent No.: US 6,752,820 B1
(45) Date of Patent: Jun. 22, 2004

(54) MEDICAL CLAMP

(76) Inventor: Michael J. Hafemann, 1913 Cypress St., Stevens Point, WI (US) 54481

( * ) Notice: Subject to any disclaimer, the term of this patent is extended or adjusted under 35 U.S.C. 154(b) by 15 days.

(21) Appl. No.: 10/194,472

(22) Filed: Jul. 15, 2002

(51) Int. Cl.$^7$ ................................................ A61B 17/00
(52) U.S. Cl. ....................................................... 606/203
(58) Field of Search ................................ 606/201, 202, 606/203, 151, 157, 204

(56) References Cited

U.S. PATENT DOCUMENTS

| | | | |
|---|---|---|---|
| 3,059,645 A | 10/1962 | Hasbrouck et al. | |
| 3,628,536 A | * 12/1971 | Glesne | ........................ 606/203 |
| 5,234,459 A | * 8/1993 | Lee | ............................. 606/203 |
| 5,269,803 A | 12/1993 | Geary et al. | ................. 606/201 |
| 5,695,520 A | * 12/1997 | Bruckner et al. | ............ 606/201 |
| 6,074,368 A | 6/2000 | Wright | ........................ 604/179 |

* cited by examiner

*Primary Examiner*—Kevin T. Truong
(74) *Attorney, Agent, or Firm*—Russell L. Johnson, Patent Agent

(57) ABSTRACT

A one piece arm encircling dialysis clamp formed of a plastic material that is firm in thick sections and elastic in thin sections, The clamp has smooth pressure applying head for applying direct pressure to the openings to blood vessels after the dialysis needles and tubes are removed. The clamp is provided with an integral arm encircling elastic band that is provided with a multiplicity of orifices that can engage projections at the fop surface of the clamp to provide an adjustable size clamp that is self-repositioning. The clamp is of unitary construction and has geometries that permit ready cleaning and sanitizing for reuse.

9 Claims, 2 Drawing Sheets

MEDICAL CLAMP

BACKGROUND OF THE INVENTION

1. Field of the Invention

In medical technology a mechanism for closing off a tubular vessel in the body is called a clamp.

This invention relates to a clamp that is applied to a limb for the purpose of closing a blood vessel or blood vessels of an arm or leg that are open to the surface.

More specifically, this invention relates to a clamp that encircles a limb and applies local pressure to blood vessels that are open to the surface for the purpose of effecting a stoppage of bleeding by the method commonly referred to as direct pressure.

Still more specifically this invention relates to the clamp described above wherein the clamp is particularly well suited for applications involving the closing of blood vessels of dialysis patients after the needles have been removed from the blood vessels of the patient.

Clamps that encircle a limb and apply direct pressure to blood vessels should do so while not shutting off circulation of blood to the ends of the extremity to which the clamp is applied.

In dialysis, tubes are inserted into a vein and an artery either directly into the blood vessels or by way of a surgical implant and blood is circulated from the artery and through a dialysis machine for the purpose of cleansing the blood after which the blood is returned to a vein.

The process of dialysis takes several hours and often needs to be repeated several times a week. Because of the duration of the dialysis, and the size of the needle used, the opening through the skin can become enlarged and difficult to close and may require an extended period of time before direct pressure can affect a closure of the blood vessel. The patient who has been attached to a dialysis machine for several hours is understandably in need of moving the limb to which the clamp is applied. A successful clamp must be able to accommodate to a limited amount of movement of the limb without moving from position over the opening or openings or losing its clamping pressure.

2. Description of the Related Art

Prior art clamps of the type contemplated by this invention are deficient in one or more of the following attributes.

Because of the number of times a clamp is employed on a dialysis patient the disposal of the clamp after a single use is not economically preferred. Therefore a successful clamp must be made of durable material that can repeatedly be cleaned and/or disinfected.

Because bleeding is often present before the clamping becomes effective, the successful clamp must be made of a smooth nonabsorbent material and be free of recesses into which blood or other contaminants may enter and be difficult to remove.

Because the patient in moving a limb will cause the limb to expand or contract, the band that encircles the arm must be accommodating to the expansion or contraction of the limb without losing position or pressure over the skin openings.

Because the direct pressure method in order to be effective must hold the sides of the opening in position and in alignment with each other until the closure knits shut, it is critical that the opening not be distorted during closure. Distortion of the opening might cause stresses in the newly closed vessel and result in reopening of the vessel after the pressure is removed.

Because the pressure is to be applied locally and frequently and for significant periods of time, it is critical that the perimeter of the pressure-applying portion of the clamp and the band that secures it be smooth and non-irritating, thereby avoiding damage to the skin or the blood vessels of the patient.

The most closely related art is found to have adjustable bands that encircle a limb and generally provide a positioning or holding function for catheters and intravenous needles. The prior art can be said to have one or more attributes in common with the instant invention, but none of the prior art provides the same means operating in the same mode to achieve the same ends as that of the instant invention.

U.S. Pat. No. 5,269,803 to Geary teaches a disposable one-piece hemostasis pressure clamp having a central channel defined by a pair of cheeks and a ridge formation formed of non-elastic plastic.

U.S. Pat. No. 3,059,645 to Hasbrouck et al teaches a unitary adjustable clamp for holding intravenous needles wherein the clamp is provided with projections that are engageable with openings spaced apart along a strap that encircles a part of the anatomy of the user.

U.S. Pat. No. 6,074,368 to Wright teaches a catheter holder that has a disk shape.

BRIEF DESCRIPTION OF THE INVENTION

A direct pressure clamp having a pressure applying head formed integral with a limb encircling band and formed of a firm elastomeric material wherein the head is provided with a broad upper gripping plate and an integral smaller pressure applying plate and an upper surface of the gripping plate is provided with at least one projection that is engageable with elastically deformable orifices defined by the band at spaced apart intervals along the limb encircling band.

DETAILED DESCRIPTION OF THE INVENTION

Figure 1:
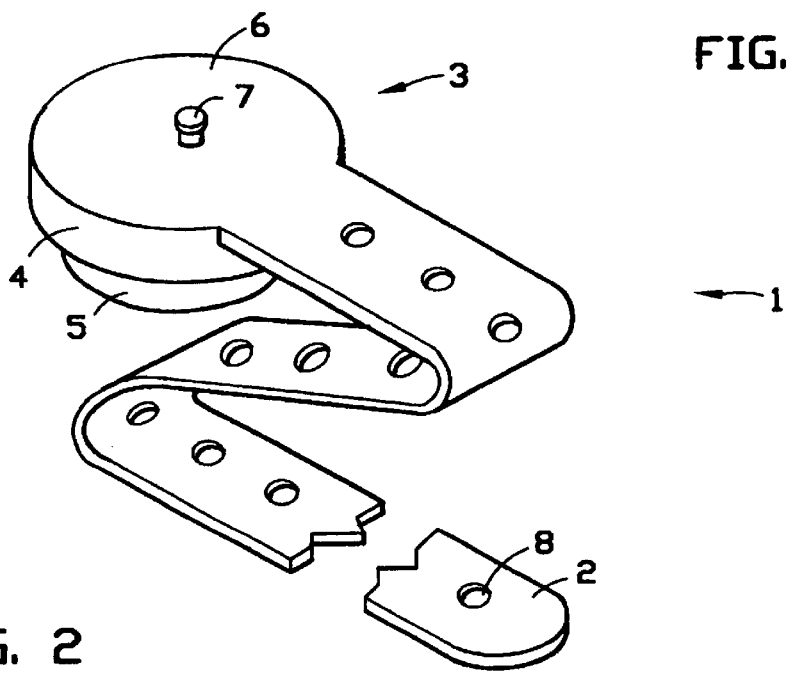
FIG. 1 is a perspective view of a pressure clamp made according to this invention.

In the drawings like numbers refer to like objects and the proportions of some elements have been changed to facilitate illustration.

Figure 2:
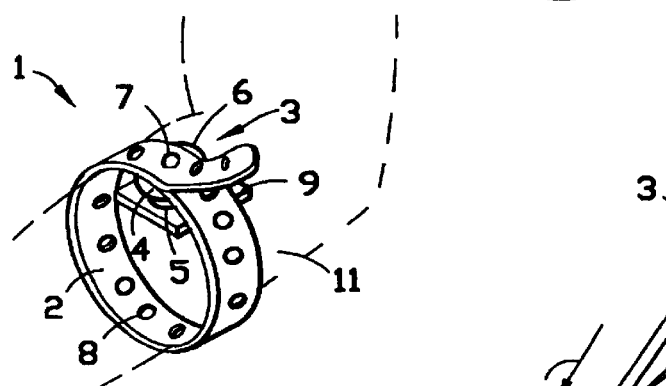
FIG. 2 is a perspective view of the clamp of claim 1 holding a dressing pad over a blood vessel of an arm.
Figure 3:
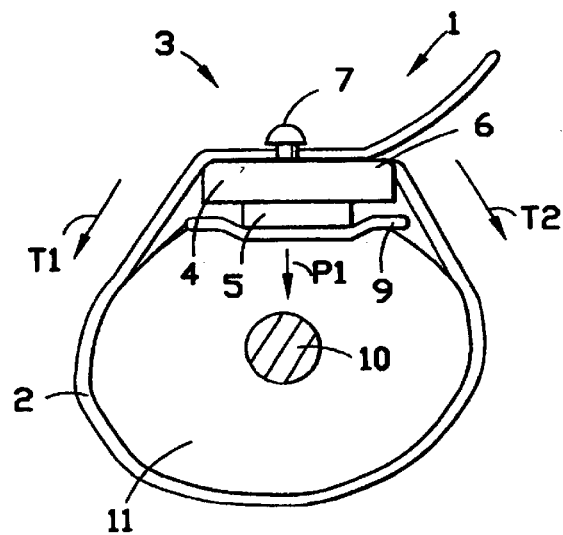
FIG. 3 is a sectioned elevation view of the clamp of claim 1 showing how the clamp applies pressure to the blood vessel while protecting the surrounding area from contamination and injury.

Referring now to FIGS. 1 through 3 wherein a preferred embodiment of the invention is shown. One-piece pressure clamp 1 is provided with an elastic limb-encircling band 2 and a pressure applying gripping head 3 having a broad upper gripping plate 4 and smaller pressure applying plate 5. Top surface 6 of gripping plate 4 is provided with a projection 7, which is engageable with elastically deformable orifices 8 in band 2.

Clamp 1 is preferably formed in a single mold and of a firm elastomeric material such as CL 4998-50 produced by the PolyOne Corp. of Cleveland, Ohio, under the brand name of 50 Duro Cream and having a durometer between 45 and 65. Elastomerics have a general property of being resilient but firm in thicker sections and being elastic in thinner sections. Band 2 which is formed integral with head 3 and is molded to have a width and thickness to provide the band with the desired elasticity, for example, 0.75 inches wide by 0.040 inches thick, to hold head 3 in position and to allow orifices 8 to be elastically deformed to engage projection 7 of head 3. It should be understood that head 3, band 2 and projection 7 could be formed separately and bonded by means such as adhesive bonding or fusion or chemical welding to form a seamless unitary assembly.

In use, it is preferred that a dressing 9 of absorbent material such as gauze or sponge be applied directly to the wound to absorb any blood that might appear in the area to be clamped and to cushion the skin in the area of clamping.

When used in situations wherein the clamping pressure will be sustained for extended periods the clamp must maintain pressure and position during limited movement of the limb to which it is attached and permit circulation in the limb by only clamping off blood flow under the pressure point as under pressure plate 5. As shown in FIG. 2 and exaggerated for the sake of illustration in FIG. 3, pressure plate 5 presses the clamping area towards the underlying bone 10. Band 2 is sufficiently wide so that the tension in band 2 is distributed over a sufficiently wide area of limb 11 so that the restriction of blood flow is limited only in the clamping area.

Referring specifically now to FIG. 3 wherein the proportions of clamp 1 and limb 11 are exaggerated to illustrate that by attaching tensioned band 2 to projection 7 on top surface 6 the tensions in band 2 to either side of clamp 1 are substantially equal and the tension vectors T1 and T2 are directed at substantially the same angle to top surface 6 so that the resultant pressure vector P1 is directed towards bone 1 0. It is critical in a direct pressure clamp of the type contemplated by this invention that when the clamp is applied to a limb of a patient that the tension vectors in the elastic band are balanced so that the pressure vector is directed towards an underlying bone. The provision of a broad upper gripping plate 4 is to provide an aid to positioning clamp 1 and also serves to limit the degree that clamp 1 can rotate away from directing the pressure on pressure applying plate 5 towards underlying bone 10 as might otherwise momentarily occur during the movement of a limb so that clamp 1 is substantially self-repositioning.

The above disclosures are enabling and would permit one skilled in the art to make and use the clamp of this invention without undue experimentations. This invention admits of variants of the clamp of FIGS. 1 through 3 that are within the scope of this invention. Representative variants are illustrated in FIGS. 4 through 6.

Figure 4:
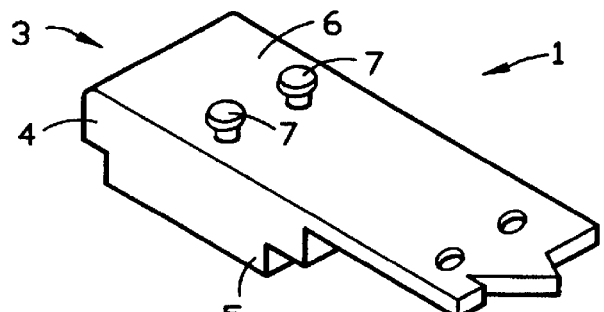
FIG. 4 is a perspective view of a preferred embodiment of the clamp of this invention.

In FIG. 4, clamp 1 has an upper gripping plate 4 that is rectangular in shape and a lower pressure applying plate 5 that is rectangular in shape and top surface 6 is provided with two projections 7 that are in transverse alignment with head 3 and band 2 is provided with two rows of orifices 8 that are engageable with projections 7.

Figure 5:
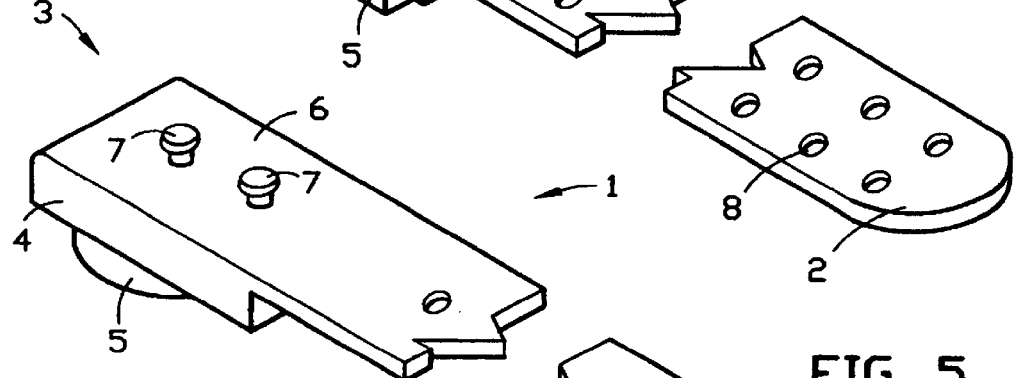
FIG. 5 is a perspective view of another preferred embodiment of the clamp of this invention taken from above.

In FIG. 5, clamp 1 has an upper gripping plate 4 that is rectangular in shape and a lower pressure applying plate 5 that is circular in shape and top surface 6 is provides with two projections 7 that are in longitudinal alignment with head 3 and band 2 is provided with one row of orifices 8 that are engageable with projections 7.

Figure 6:
FIG. 6 is a perspective view of another preferred embodiment of the clamp of this invention taken from below.

In FIG. 6, clamp 1 has an upper gripping plate 4 that is rectangular in shape and a lower pressure applying plate 5 that is circular in shape similar to those of FIG. 5 and top surface 6 is provided with two projections 7 (not shown) that are in transverse alignment with head 3 and band 2 is provided with two rows of orifices 8 that are engageable with projections 7 similar to what is disclosed in relation to FIG. 4.

It can be seen from the variants disclosed above that this invention admits of numerous combinations of materials, constructions, and geometries the disclosure, illustration, and claiming of which would greatly multiply the drawings and claims and cause the specifications to become prolix. Therefore, it should be understood that the scope of this invention should not be limited to the scope of the embodiments disclosed above but should only be limited by the scope of the appended claims and all equivalents thereto that would be made apparent thereby to one skilled in the art.

What is claimed is:

1. A direct pressure clamp comprising:

A smooth firm pressure applying head formed integral with an elastic limb encircling band and formed of a firm elastomeric material wherein the head is provided with a broad upper gripping plate and an integral smaller pressure applying plate and an upper surface of the gripping plate is provided with at least one projection that is engageable with elastically deformable orifices defined at spaced apart intervals along the limb encircling band.

2. The direct pressure clamp of claim 1 wherein the pressure applying plate is in the form of a disk and the gripping plate is in the form of a disk.

3. The direct pressure clamp of claim 1 wherein the pressure applying plate is in the form of a disk and the gripping plate is in the form of a rectangle.

4. The direct pressure clamp of claim 1 wherein the pressure applying plate is in the form of a rectangle and the gripping plate is in the form of a rectangle.

5. The clamp of claim 1 wherein the clamp is a one-piece clamp.

6. The clamp of claim 1 wherein the clamp is of a unitary construction.

7. The clamp of claim 1 wherein, in use, tension vectors in the limb encircling band to each side of the top surface are balanced providing said head with a pressure vector that is directed towards a central bone of the limb to which it is attached.

8. The clamp of claim 1 wherein, in use, the broad upper gripping plate serves to limit the degree of rotation permitted to the head and thereby renders the clamp substantially self-repositioning.

9. A direct pressure clamp comprising:

A firm flat smooth pressure applying head formed integral with an elastic limb encircling band and formed of a firm elastomeric material wherein the head is provided with a broad upper gripping plate and an integral smaller pressure applying plate and an upper surface of the gripping plate is provided with at least one projection that is engageable with elastically deformable orifices defined at spaced apart intervals along the limb encircling band, and the clamp is a one-piece clamp, wherein, in use, the tension vectors in the band to each side of the top surface are balanced providing said head with a pressure vector that is directed towards a central bone of the limb to which it is attached, and wherein, in use, the broad upper gripping plate serves to limit the degree of rotation permitted to the head and thereby renders the clamp substantially self repositioning.

\* \* \* \* \*